US009220769B2

United States Patent
Townsend

(10) Patent No.: US 9,220,769 B2
(45) Date of Patent: Dec. 29, 2015

(54) COMPOSITION

(71) Applicant: Isis Innovation, Ltd., Oxford (GB)

(72) Inventor: Alain Townsend, Oxford (GB)

(73) Assignee: Isis Innovation, Ltd., Oxford (GB)

( * ) Notice: Subject to any disclaimer, the term of this patent is extended or adjusted under 35 U.S.C. 154(b) by 0 days.

(21) Appl. No.: 14/346,669

(22) PCT Filed: Sep. 21, 2012

(86) PCT No.: PCT/GB2012/052341
§ 371 (c)(1),
(2) Date: Mar. 21, 2014

(87) PCT Pub. No.: WO2013/041877
PCT Pub. Date: Mar. 28, 2013

(65) Prior Publication Data
US 2014/0242103 A1    Aug. 28, 2014

(30) Foreign Application Priority Data

Sep. 23, 2011   (GB) .................................. 1116416.7

(51) Int. Cl.
| | | |
|---|---|---|
| *A61K 39/145* | (2006.01) | |
| *C12N 7/00* | (2006.01) | |
| *A61K 39/12* | (2006.01) | |
| *C07K 14/005* | (2006.01) | |
| *A61K 39/00* | (2006.01) | |

(52) U.S. Cl.
CPC .............. *A61K 39/145* (2013.01); *A61K 39/12* (2013.01); *C07K 14/005* (2013.01); *C12N 7/00* (2013.01); *A61K 2039/5254* (2013.01); *A61K 2039/58* (2013.01); *C12N 2760/16022* (2013.01); *C12N 2760/16062* (2013.01); *C12N 2760/16122* (2013.01); *C12N 2760/16134* (2013.01); *C12N 2760/16162* (2013.01)

(58) Field of Classification Search
None
See application file for complete search history.

(56) References Cited

PUBLICATIONS

Weltman et al (BBRC 352: 177-180, 2007).*
Abdel-Moneim et al (Archives of Virology 154:1559-1562, 2009).*
Townsend et al (Nature 324:375-377, 1986).*
Gething et al (Nature 300:598-603, 1982).*
Sekikawa et al (PNAS UAS 80:3563-3567, 1983).*
International Search Report and Written Opinion mailed on Mar. 11, 2013 for Application No. PCT/GB2012/052341; 13 pages.
Powell Tj et al. "Pseudotyped Influenza A Virus as a Vaccine for the Induction of Heterotypic Immunity." J Virol 86(24):13397-13406, 2012.
Stech J et al. "A new approach to an influenza live vaccine: modification of the cleavage site of hemagglutinin." Nat Med 11(6):683-689, 2005.

* cited by examiner

*Primary Examiner* — Mary E Mosher
(74) *Attorney, Agent, or Firm* — Wilmer Cutler Pickering Hale and Dorr LLP

(57) ABSTRACT

The present invention provides a modified influenza virus wherein the RNA of the haemagglutinin gene has been modified such that the haemagglutinin signal sequence is not expressed and the virus produces a haemagglutinin protein that lacks a functional signal sequence. The invention further provides composition comprising the modified virus and uses of the modified virus.

19 Claims, 11 Drawing Sheets

S- HA Influenza

A del to create frame shift

ATG

5' UTR 32 bp

TAG

Figures 2A, 2B, 2C, 2D:
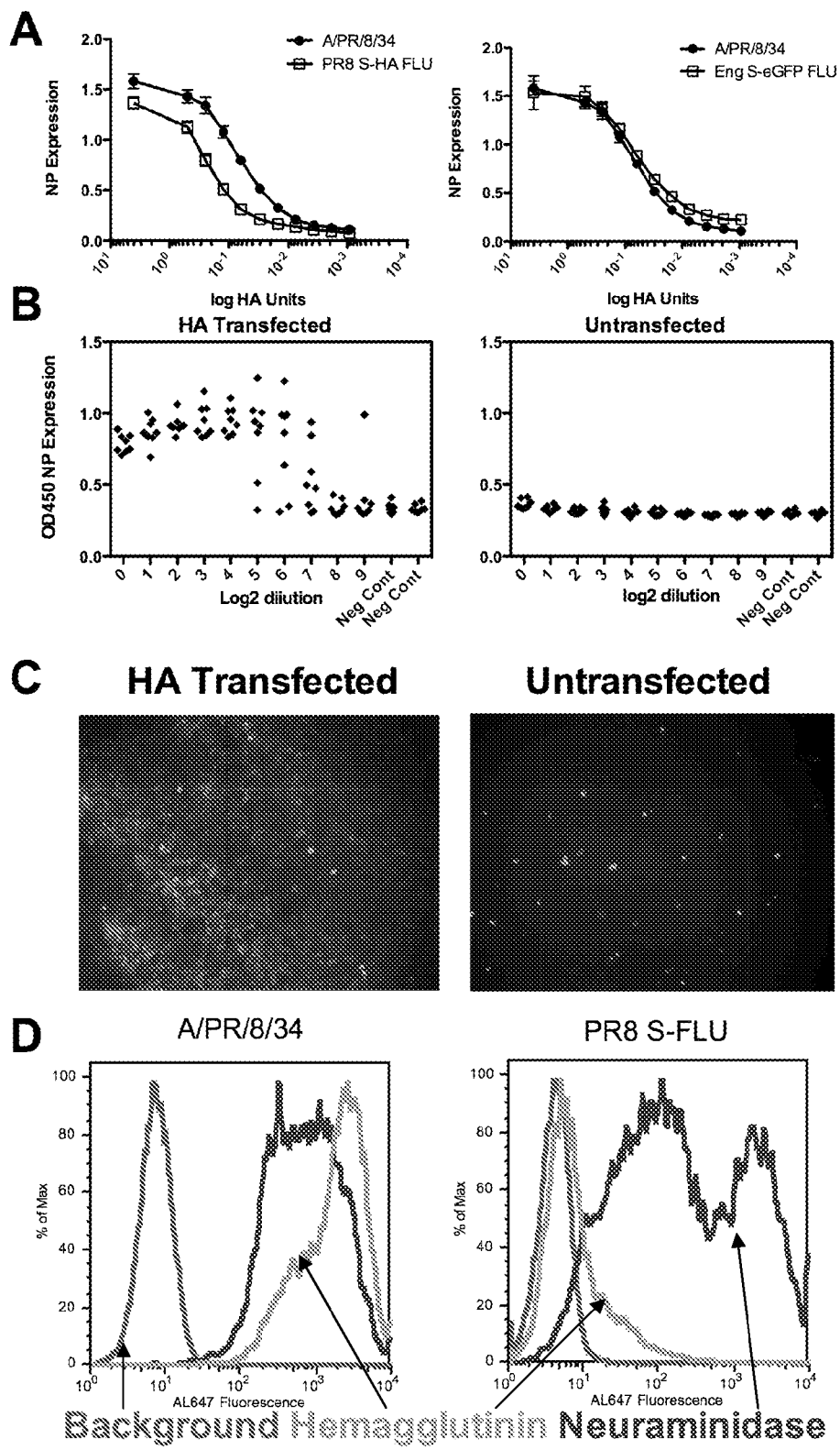

GCGGCCGCCACCATG
NotI site-New Kozac

Cleavage site inactivated

Arg
AGA

CAG
Gln

3' UTR 45bp

5' UTR 32 bp

NotI

S-eGFP Influenza

STOP

EcoRI

3' UTR 45bp

Figure 1A

```
          10        20        30        40        50        60
  AGCAAAAGCAGGGGAAAATAAAAACAACCAAAAATGAAGGCAAACCTACTGGTCCTGTTAT
  :::::::::::::::::::::::::::::::::   ::::::::::::::::::::::::
  AGCAAAAGCAGGGGAAAATAAAAACAACCAAATAGAAGGCAAACCTACTGGTCCTGTTAT
          10        20        30        40        50        60

70        80                            90       100
  GTGCACTTGCAGCTGCAGATCCA------------GACACAATATGTATAGGCTACCA
  :::::::::::::::::::::::              ::::::::::::::::::::::
  GTGCACTTGCAGCTGCAGATCCAGCGGCCGCCACCATGGACACAATATGTATAGGCTACCA
          70        80        90       100       110       120

1010      1020      1030      1040      1050      1060
  CAGTGCCAAATTGAGGATGGTTACAGGACTAAGGAACATTCCGTCCATTCAATCCAGAGG
  ::::::::::::::::::::::::::::::::::::::::::::::::::::::::   ::
  CAGTGCCAAATTGAGGATGGTTACAGGACTAAGGAACATTCCGTCCATTCAATCCCAGGG
         1030      1040      1050      1060      1070      1080
```

Figure 1B

Figure 4

SEQUENCE LISTING

```
<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcggccgcca ccatg                                                          15

<210> SEQ ID NO 2
<211> LENGTH: 106
<212> TYPE: DNA
<213> ORGANISM: Influenza A virus

<400> SEQUENCE: 2
agcaaaagca ggggaaaata aaaacaacca aaatgaaggc aaacctactg gtcctgttat         60
gtgcacttgc agctgcagat gcagacacaa tatgtatagg ctacca                       106

<210> SEQ ID NO 3
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
agcaaaagca ggggaaaata aaaacaacca aatagaaggc aaacctactg gtcctgttat         60
gtgcacttgc agctgcagat gcgcggccgc caccatggac acaatatgta taggctacca       120

<210> SEQ ID NO 4
<211> LENGTH: 60
<212> TYPE: DNA
<213> ORGANISM: Influenza A virus

<400> SEQUENCE: 4
gagtgccaaa ttgaggatgg ttacaggact aaggaacatt ccgtccattc aatccagagg         60

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 5
gagtgccaaa ttgaggatgg ttacaggact aaggaacatt ccgtccattc aatcccaggg    60
```

COMPOSITION

This application is a U.S. National Phase Application under 35 U.S.C. §371 of International Patent Application No. PCT/GB2012/052341 filed Sep. 21, 2012, and published as WO 2013/041877 on Mar. 28, 2013, which claims the benefit of priority of GB Application No. 1116416.7, filed Sep. 23, 2011, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Aug. 10, 2015, is named 2001630.122_US1_SL.txt and is 1,440 bytes in size.

The present invention relates to modified influenza viruses, and to their use in eliciting an immune response, and in particular, to their use in eliciting a protective immune response.

Influenza remains a constant worldwide threat to human health. There are several potential strategies for the development of vaccines to protect humans against influenza viruses, including (1) inactivated virus vaccine; (2) subunit vaccine that uses purified haemagglutinin and/or neuraminidase components; and (3) live attenuated vaccines. While inactivated influenza viruses have been available for many years, such vaccines provide only limited protection. Protein subunits have also been available for many years, however they are expensive to produce and display little cross reactivity between strains. To date live attenuated viruses have been shown to produce the best protection, however the problem of safety remains an issue.

Previous efforts to provide a safe, live attenuated influenza vaccine have focussed primarily on cold-adapted influenza viruses. Such attenuated viruses are obtained by extensively passaging the virus at low temperatures, such that the virus becomes adapted to grow at low temperature. Eventually the viruses lose their ability to replicate at higher temperatures. The replication of such cold-adapted viruses is only slightly restricted in the cooler upper respiratory tract, but highly restricted in the warmer lower respiratory tract, the major site of disease-associated pathology. Sequence comparisons between wild-type and cold-adapted influenza viruses have revealed both silent mutations and non-silent mutations leading to amino acid changes in the coding regions of several gene segments. Most amino acid changes were found to be the result of point mutations. The genetic instability of point mutations, and the degree of immunogenicity of cold-adapted influenza viruses, remains a potential problem for the use of cold-adapted influenza viruses as vaccines for worldwide general use.

Another approach to obtaining live attenuated influenza viruses which has been investigated is the construction of chimeric influenza viruses in which a non-coding region of an influenza virus genomic segment is substituted by a non-coding region from a genomic segment of an influenza virus of a different type. Such attenuated chimeric A/B influenza viruses are discussed, for example, in Muster et al., Proc. Natl. Acad. Sci. USA (1991) 88, 5177-5181, Luo et al., J. Virology (1992) 66 4679-4685 and Bergmann and Muster, J. General Virology (1995) 76 3211-3215.

Ideally, a live vaccine should be safe and effective in providing protection, and cost-effective in production. For safety, the vaccine should be sufficiently attenuated and that it would not cause clinical symptoms even at a high dose of vaccination. For effective protection, the vaccine, even at low dose of vaccination, should be immunogenic enough to provide sufficient protection from virulent infection. For cost-effective production the vaccine strain should be cost effective to produce.

In practice, however, it is difficult to generate a vaccine strain that satisfies all three requirements—safety, efficacy and the cost-effectiveness. Usually, attenuation (providing safety) results in poor growth (at the expense of cost-effectiveness), and renders the virus less immunogenic (requiring high dose of vaccination).

In addition to the different types of vaccine there are three known types of influenza virus, these are designated as types A, B and C.

Each of the influenza virus types has many strains. The genome of an influenza virus is a segmented genome consisting of a number of negative sense RNAs (8 in the case of types A and B and 7 in the case of type C), which encode (in the case of type A) 10 polypeptides: the RNA-directed RNA polymerase proteins (PB1, PB2 and PA) and nucleoprotein (NP) which form the nucleocapsid, the matrix proteins (M1, M2), two surface glycoproteins which project from the lipoprotein envelope (haemagglutinin (HA) and neuraminidase (NA)) and the non-structural proteins NS1 and NS2. The majority of the genomic RNA segments are monocistronic. Thus, in the case of an influenza virus of type A, 6 of the 8 genomic RNA segments are monocistronic and encode HA, NA, NP and the viral polymerase proteins, PB1, PB2 and PA.

Influenza A viruses are responsible for the major pandemics of influenza in the last century and are also the causative agents for most of the annual outbreaks of epidemic influenza.

There are many different influenza A virus subtypes, differing in the nature of the haemagglutinin and neuraminidase glycoproteins on their surface. Sixteen haemagglutinins (H1 to H16) and nine neuraminidases (N1 to N9) have been identified. Among these, H1, H2 and H3 virus subtypes have been identified in humans, specifically the H1N1, H2N2 and H3N2 viruses. Virus subtypes are distinguishable serologically, which means that antibodies to one subtype do not properly react with another subtype. Besides humans influenza viruses infect a variety of hosts including swine, avian and equestrian species. Among these, aquatic birds appear to serve as a major reservoir of influenza A viruses; indeed, all human influenza virus subtypes circulate also in these wild birds. During recent outbreaks of avian influenza, there have been occasional transmissions of H5N1, H7N7 and H9N2 viruses to humans (Proc. Natl. Acad. Sci. USA 101, 8156-8161, 2004). Besides influenza A subtypes, influenza B virus also infects humans especially very young children. For this reason the current influenza vaccine stipulates the use of three different components (A/H1N1, A/H3N2 and B virus) in a trivalent vaccine formula.

Because of high mutation rates of the RNA genome of the influenza viruses, different strains emerge almost every year and cause annual influenza epidemics. Antigenic drift involves minor changes in the haemagglutinin, neuraminidase and possibly also other viral antigens, that occur due to mutations in the viral genome, these mutations result in amino acid substitution in antigenic sites. These changes may render the new strain different enough to at least partially avoid the immunity induced by previous strains.

Since influenza virus genomes are segmented, influenza viruses frequently undergo drastic changes, also referred to as antigenic shift, by genetic reassortment between different virus strains. This means that a virus with a new haemagglutinin (and/or neuraminidase) is introduced into the human population. If this results in an especially virulent strain the infection would spread rapidly and cause high morbidity and mortality among the entire population, including young healthy people. The human population has experienced at least three major influenza pandemics in the 20th century. The Spanish influenza (caused by an H1N1 influenza A virus) in 1918, Asian flu in 1957 (caused by an H2N2 influenza A virus) and Hong Kong flu in 1968 (caused by an IT3N2 influenza A virus). Moreover, in the last decade there have been numerous reports of human infection by avian influenza viruses (including H5N1, H7N7 and H9N2 viruses). This supports the concept that a new pandemic influenza may be derived from avian virus reservoirs. Avian influenza viruses may be directly transmitted to humans, which probably occurred in the case of the 1918 Spanish flu virus. The possibility of direct transmission of an avian influenza virus to humans became evident for the first time during the H5N1 outbreak in Hong Kong in 1997.

An aim of the present invention is to provide one or more compositions which can be used to elicit a safe and protective immune response against the influenza virus, and in particular, influenza A.

According to a first aspect, the present invention provides a modified influenza virus wherein the RNA of the haemagglutinin gene has been modified such that the haemagglutinin signal sequence is not expressed and the virus produces a haemagglutinin protein that lacks a functional signal sequence.

The modified RNA encoding the haemagglutinin signal sequence is preferably retained in a mutated form in the modified virus. The modified RNA is preferably retained as it has other functions such as in viral packaging, unrelated to the expression of the haemagglutinin signal sequence.

In a wild type virus the haemagglutinin signal sequence is typically a 17 amino acid peptide located at the N terminal end of the haemagglutinin protein. The signal sequence is required for folded haemagglutinin to be placed at the cell surface. Without this sequence the synthesised haemagglutinin protein remains in the cytosol and is rapidly degraded. The resulting peptides are then bound to class I MHC molecules and presented to the host immune system.

Preferably in the modified virus the RNA is modified such that the RNA corresponding to the haemagglutinin signal sequence has at least about 60%, 65%, 70%, 75%, 80%, 85%, 90%, 95% or more sequence homology with the wild type haemagglutinin signal sequence RNA.

Reference to percentage homology relates to the percent identity between two aligned sequences. The percent identity refers to the residues in two nucleic acids which are the same, when the sequences are aligned for maximum correspondence and when introns, inversions and translocations are accounted for. The percent identity between aligned sequences can be established by using well-established tools (such as the BLAST algorithm—Basic Local Alignment Search Tool; Altschul et al., (1990) J Mol Biol. 215:403-10)

Removal of the signal sequence from the haemagglutinin protein prevents the haemagglutinin protein being transported to the cell virus surface and thus prevents viral replication; however the haemagglutinin protein without the signal sequence is still processed by the cell and presented to the host human system thus retaining its antigenicity, in particular in terms of a T-cell response.

Townsend et al in Nature (1986) Vol 324, pg 575-577 demonstrated that the expression of a signal deleted haemagglutinin protein in influenza viruses resulted in a T-cell response to the haemagglutinin, thereby demonstrating that the haemagglutinin does not need to be on the cell surface to have an immunogenic effect.

Preferably modified viruses of the invention are attenuated, such that they cannot replicate, or that they replicate very inefficiently, upon infection of a human or non-human animal.

The modified virus of the present invention has the advantage that it can be produced in tissue culture and does not need to be produced using eggs as is the case with most cold activated live attenuated viruses. This means the modified virus of the invention can be produced at much lower cost.

The influenza virus may be type A, B or C, preferably the influenza virus is type A.

The modified virus may contain RNA encoding any one or more of the sixteen haemagglutinin types (H1 to H16) wherein the signal sequence is not expressed. Preferably a mutated form of the signal sequence is present.

Preferably a modified virus of the invention is capable of infecting host human or non-human animal cells and inducing a substantially complete immune response. A substantially complete immune response may include a local and systemic neutralising antibody response to the haemagglutinin and neuraminidase on the cell surface, and a cross reactive T cell response to the internal proteins of the modified virus. This breadth of immune response is advantageous compared to the narrow antibody only response observed with sub-unit vaccines.

Preferably modified virus according to the invention is produced in a cell line which provides exogenous haemagglutinin including a signal sequence which is packaged into the virus particles and allows them to infect a host.

Modified viruses of the invention are preferably produced using a cell line which produces a haemagglutinin protein including a signal sequence, the virus particles can then use this exogenously provided haemagglutinin to produce complete viral particles with haemagglutinin on the viral particle outer surface. The haemagglutinin inside the virus particle which lacks the signal sequence will be encoded by the viral RNA. Haemagglutinin on the viral particle surface is required for viral infectivity. The type of haemagglutinin on the viral particle surface may be the same or different to the type of haemagglutinin encoded by the viral genome. For example, the viral surface may display H1 but the virus may itself produce signal deleted H2. In this example an antibody response may be generated to H1 and a T-cell response may be generated to H2. In a further embodiment the viral particle may include more than one type of haemagglutinin on the viral particle surface, one of the surface expressed haemagglutinins may be the same type as the signal deleted haemagglutinin expressed by the viral genome.

By controlling the haemagglutinin displayed on the viral particle surface and the signal free haemagglutinin expressed in the viral particle the nature of the immune response generated on exposure to the modified virus can be controlled. Typically the proteins on the cell surface are responsible for the antibody response generated, and the signal free haemagglutinin in the virus generates a T-cell response. Furthermore by carefully selecting the haemagglutinin on the viral particle surface interaction with a host airway can be controlled.

A major concern about using live attenuated viruses containing a haemagglutinin gene from a potentially pandemic strain (not presently circulating in man) is that in rare cases of co-infection of a host with a live attenuated virus and a seasonal viral strain, a reassortment of genes may result such that the haemagglutinin gene from the live attenuated virus could become incorporated into the seasonal strain to form a new epidemic or pandemic strain; the exact opposite to what was intended.

The modified influenza virus of the present invention is preferably configured to prevent this happening. The loss of the signal sequence from the expressed haemagglutinin protein means that even if the genes is reassorted into another strain it would result in a strain that was unable to replicate due to a lack of functional haemagglutinin on the viral particle surface.

Preferably a modified influenza virus of the present invention comprises at least the following i) a mutation in the original start codon for translation of the haemagglutinin gene, which would normally produce a haemagglutinin protein with a signal sequence, such that it is no longer a start codon; and ii) the introduction of a new start codon to drive translation of the haemagglutinin gene just after the signal sequence. The new start codon may be contained within a newly inserted Kozak sequence.

The modified influenza virus may also comprise additional modifications to the haemagglutinin gene to further prevent any back mutations from producing a haemagglutinin protein with a signal sequence, thereby further minimizing the associated risks of introduction into the environment via reassortment into a seasonal influenza strain. Further mutations may include one or more of i) a frameshift mutation in the RNA encoding the signal sequence downstream of the mutated start codon, this would mean that if for some reason the mutated start codon was mutated back to be a start codon then the haemagglutinin produced would be non-functional; and ii) removal of one or more cleavage sites in the haemagglutinin protein which are required for presentation of the haemagglutinin protein on the cell surface.

Together these mutations reduce the likelihood that the haemagglutinin gene could mutate back to the functional full length haemagglutinin gene encoding a haemagglutinin protein and signal sequence.

The modifications to the haemagglutinin gene may include one or more of the following:
i) mutation of nucleotide 33 (A in the WT A/PR/8/34 haemagglutinin gene) and nucleotide 34 (T in the WT A/PR/8/34 haemagglutinin gene) such that the start codon is removed. The mutation may be nucleotide 33 A to T and nucleotide 34 T to A;
ii) deletion of nucleotide 83 (A in the WT A/PR/8/34 haemagglutinin gene);
iii) insertion of a Kozak sequence in the place of nucleotide 83;
iv) mutations of one or more of nucleotides 1063, 1064 and 1065 (AGA in the WT A/PR/8/34 haemagglutinin gene) to remove the cleavage site. The mutation may be 1063 A to C, 1064 G to A or 1065 A to G.

The nature of the haemagglutinin gene in the modified virus is such that if it did reassort into another flu strain then the sequence is disrupted such that the arising influenza strain would be unable to replicate.

According to another aspect the invention provides a method of preparing a modified influenza virus according to the first aspect of the invention comprising i) providing a host cell that expresses haemagglutinin with a signal sequence from a eukaryotic mRNA; and ii) providing the viral genomic nucleic acid segments for the modified virus under conditions whereby the segments are packaged into a viral particle. Preferably the presence of the host provided haemagglutinin protein with signal sequence allows the modified influenza virus produced to replicate and proliferate. The viral genomic nucleic acid segments may be provided in the host cell using one or more plasmids. This may use the standard methodology developed by Fodor et al (1999) Journal of Virology 73:9697-9682. The plasmids used may include one to make the full length haemagglutinin protein so that the packaged virus can begin to replicate. The transfections may be done in 293T cells and then the rescued virus may be grown in MDCK or a subline MDCK-SIAT1 transfected with the full length haemagglutinin gene which will coat the virus particles. The haemagglutinin gene used in the transfection may be synthesised with codons optimised for eukaryotic expression. This has two advantages—it increases the amount of haemagglutinin which helps replication and the altered sequence (encoding the same protein) is very unlikely to be able to contribute to back mutations in the vRNA encoding the S-HA.

According to a further aspect, the present invention provides an immunogenic composition comprising a modified influenza virus according to the first aspect of the invention.

Preferably the immunogenic composition is capable of eliciting an immune response when administered to a human or non-human animal. Preferably the immune response elicited is both an antibody response and a T-cell response. The surface haemagglutinin may prime the B cell response to the inoculating dose, and the intracytoplasmic haemagglutinin expressed from the viral genome can then be used to optimise the T-cell response. Preferably all other viral proteins are also expressed inside the cells to optimise the cross-reactive lytic T-cell response.

The immune response may be therapeutic and/or prophylactic. The immunogenic composition may be a vaccine.

The composition may further comprise an adjuvant, wherein an adjuvant enhances the protective efficacy of the composition. Suitable adjuvants will be well known to those skilled in the art, and may include emulsifiers, muramyl dipeptides, avridine, MF59, aqueous adjuvants such as aluminum hydroxide, chitosan-based adjuvants, monophosphoryl Lipid A and any of the various saponins, oils, and other substances known in the art, such as Amphigen, LPS, bacterial cell wall extracts, bacterial DNA, CpG sequences, synthetic oligonucleotides and combinations thereof. Other suitable adjuvants can be formed with an oil component, such as a single oil, a mixture of oils, a water-in-oil emulsion, or an oil-in-water emulsion. The oil may be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed Mycobacterium sp.

The composition may also comprise polymers or other agents to control the consistency of the composition, and/or to control the release of the protein from the composition.

The composition may also comprise other agents such as diluents, which may include water, saline, glycerol or other suitable alcohols etc; wetting or emulsifying agents; buffering agents; thickening agents for example cellulose or cellulose derivatives; preservatives; detergents; antimicrobial agents; and the like.

Preferably the active ingredients in the composition are greater than 50% pure, usually greater than 80% pure, often greater than 90% pure and more preferably greater than 95%, 98% or 99% pure. With active ingredients approaching 100% pure, for example about 99.5% pure or about 99.9% pure, being used most often.

A composition according to the invention may be for oral, systemic, parenteral, topical, mucosal, intramuscular, intravenous, intraperitoneal, intradermal, subcutaneous, intranasal, intravaginal, intrarectal, transdermal, sublingual, inhalation or aerosol administration. Preferably the composition is for intranasal administration.

Preferably the immune response elicited by a composition of the invention is effective against one or more influenza strains.

Preferably the immune response elicited by the composition of the invention affects the ability of the influenza virus to infect an immunised animal. Preferably the ability of influenza to infect a human immunised with the composition of the invention is impeded or prevented. This may be achieved in a number ways. The immune response elicited may recognise and destroy influenza virus. Alternatively, or additionally, the immune response elicited may impede or prevent the replication of the influenza virus. Alternatively, or additionally, the immune response elicited may impede or the prevent influenza virus causing disease in the human or non-human animal. Preferably the immune response elicited is directed to at least influenza A.

The composition of the invention may also comprise a further one or more antigens, in addition to the modified virus. The further antigens may also be derived from an influenza virus, and may be capable of eliciting an immune response directed to the influenza virus.

The composition may be used to elicit/produce a protective immune response when administered to a subject. The protective immune response may cause the influenza virus to be killed upon infecting the subject, or it may prevent or inhibit the influenza virus from replicating and/or from causing disease.

The composition may be used as a prophylactic or a therapeutic vaccine directed to the influenza virus, and in particular to influenza A.

The composition may be used as part of a prime boost vaccination regimen. The composition may be used in an intial prime vaccination, where the boost may be with a protein antigen. This would allow time for protein to be produced, for example in an epidemic or pandemic situation, and would also reduce costs. It is much cheaper to produce a composition of the invention than to produce a protein based vaccine.

According to a further aspect, the invention provides a pharmaceutical composition comprising a virus or a composition of the invention and a pharmaceutically acceptable carrier or excipient.

Preferably the pharmaceutical composition comprises a modified influenza virus according to the invention.

Preferably the pharmaceutical composition is capable of producing a protective immune response to influenza.

The phrase "producing a protective immune response" as used herein means that the composition is capable of generating a protective response in a host organism, such as a human or a non-human mammal, to whom it is administered. Preferably a protective immune response protects against subsequent infection by an influenza virus. The protective immune response may eliminate or reduce the level of infection by reducing replication of the influenza virus, or by affecting the mode of action of the influenza virus, to reduce disease. Preferably the protective response is directed to at least influenza A.

Suitable acceptable excipients and carriers will be well known to those skilled in the art. These may include solid or liquid carriers. Suitable liquid carriers include water and saline. The proteins of the composition may be formulated into an emulsion or they may be formulated into biodegradable microspheres or liposomes.

The composition of the present invention may be used as a vaccine against infections caused by the influenza virus, in particular by influenza A. The vaccine may be administered prophylactically to those at risk of exposure to the influenza virus, and/or therapeutically to persons who have already been exposed to the influenza virus.

Preferably, if the composition is used as a vaccine, the composition comprises an immunologically effective amount of modified virus. An "immunologically effective amount" of a virus is an amount that when administered to an individual, either in a single dose or in a series of doses, is effective for treatment or prevention of infection by influenza. This amount will vary depending upon the health and physical condition of the individual to be treated and on the antigen. Determination of an effective amount of an immunogenic or vaccine composition for administration to an organism is well within the capabilities of those skilled in the art.

The composition may be arranged to be administered as a single dose or as part of a multiple dose schedule. Multiple doses may be administered as a primary immunisation followed by one or more booster immunisations. Suitable timings between priming and boosting immunisations can be routinely determined.

A composition according to the invention may be used in isolation, or it may be combined with one or more other immunogenic or vaccine compositions, and/or with one or more other therapeutic regimes.

According to a further aspect, the present invention provides the use of the modified influenza virus of the invention in the preparation of a medicament for eliciting an immune response. The medicament may be used for the prophylactic or therapeutic vaccination of subjects against influenza. The medicament may be a prophylactic or a therapeutic vaccine.

According to a yet further aspect, the invention provides a composition comprising the modified influenza virus for use in generating an immune response to influenza. The immune response may be prophylactic or therapeutic. The composition may be for use as a vaccine.

According to a still further aspect, the present invention provides a method of protecting a human or non-human animal from the effects of infection by the influenza virus comprising administering to the human or non-human animal a composition according to any other aspect of the invention. The composition may be a vaccine.

According to another aspect, the invention provides a method for raising an immune response in a human or non-human animal comprising administering a pharmaceutical composition according to the invention to the human or non-human animal. The immune response is preferably protective. The method may raise a booster response in a patient that has already been primed. The immune response may be prophylactic or therapeutic.

One way to check the efficacy of a therapeutic treatment comprising administration of a composition according to the invention involves monitoring for influenza virus infection after administration of the composition. One way to check the efficacy of a prophylactic treatment comprising administration of a composition according to the invention involves monitoring immune responses to influenza virus after administration of the composition.

According to another aspect, the invention provides the use of the modified influenza virus in the preparation of a medicament for use in the immunisation of human or non-human mammals against infection by the influenza virus.

According to a further aspect the invention provides a kit for use in inducing an immune response in an organism, comprising an immunogenic or vaccine composition according to the invention and instructions relating to administration.

In addition to their use as vaccines, compositions according to the invention may be useful as diagnostic reagents and as a measure of the immune competence of a vaccine.

It will be appreciated that optional features applicable to one aspect of the invention can be used in any combination, and in any number. Moreover, they can also be used with any of the other aspects of the invention in any combination and in any number. This includes, but is not limited to, the dependent claims from any claim being used as dependent claims for any other claim in the claims of this application.

Preferred embodiments of the present invention will now be described, merely by way of example, with reference to the following figures and examples.

FIGS. 1A and 1B—FIG. 1A is a schematic diagram of the design for the inactivation of the Hemagglutinin (HA) signal sequence to produce S-HA FLU. For eGFP expression the S-HA sequence was replaced with eGFP between the NotI site and a unique EcoR I site at position 1268, beyond the HA cleavage site. Viruses were named according to their genotype between square brackets, followed by the identity of the HA in the viral coat obtained from the transfected cells in which replication occurred. For example [S-H1(PR8)/N1 (PR8)] H1(Eng195)=S-H1and N1 vRNAs from A/PR/8/34, coat HA from A/Eng/195/2009 (pandemic H1); FIG. 1B shows the sequence of the full length A/PR/8/34 haemagglutinin (top line) compared to the mutant form in a modified virus according to the invention (S-FLU). The sequences are shown in the mRNA sense strand and the numbering of the bases is as described by Winter et al (1981) Nature 292, 72-75. FIG. 1A discloses SEQ ID NO: 1. FIG. 1B discloses SEQ ID NOS 2-5, respectively, in order of appearance.

FIG. 2A—illustrates that infection of MDCK-SIAT1 monolayer with [S-HA(PR8)/N1(PR8)] H1(PR8) generates similar levels of NP expression as wild-type A/PR/8/34. MDCK monolayers in replicates of 8 in 96 well plates were infected o/n with 4 and 0.5 HAU/well then doubling dilutions of virus.

FIG. 2B—demonstrates that the clonal expansion (detected by NP express ion) of S-FLU requires the presence of hemagglutinin expressed by the MDCK cells and added trypsin. Virus [S-H1(Eng195)/N1 (Eng195)] H1(Eng195) prepared at 1/400 of an HA unit/well then serially diluted 2 fold as noted in replicates of 8 in 96 well plates was grown in the presence of trypsin for 48 hrs.

FIG. 2C—illustrates the dependence of clonal expansion on HA expression in the monolayer shown by eGFP expression by S-FLU.

FIG. 2D—illustrates the expression of Neuraminidase but not Hemagglutinin at the surface of cells infected with PR8 S-FLU. MDCK-SIAT1 cells were infected o/n with [S-H1 (PR8)/N1(PR8)/N1(PR8)] H1(PR8) or A/PR/8/34 and then labelled by indirect immunofluorescence with monoclonal antibodies to Hemagglutinin H9-D3 Cb13 or Neuraminidase NA2-1C1. Experiments were repeated at least twice with replicates indicated.

Figure 2E:
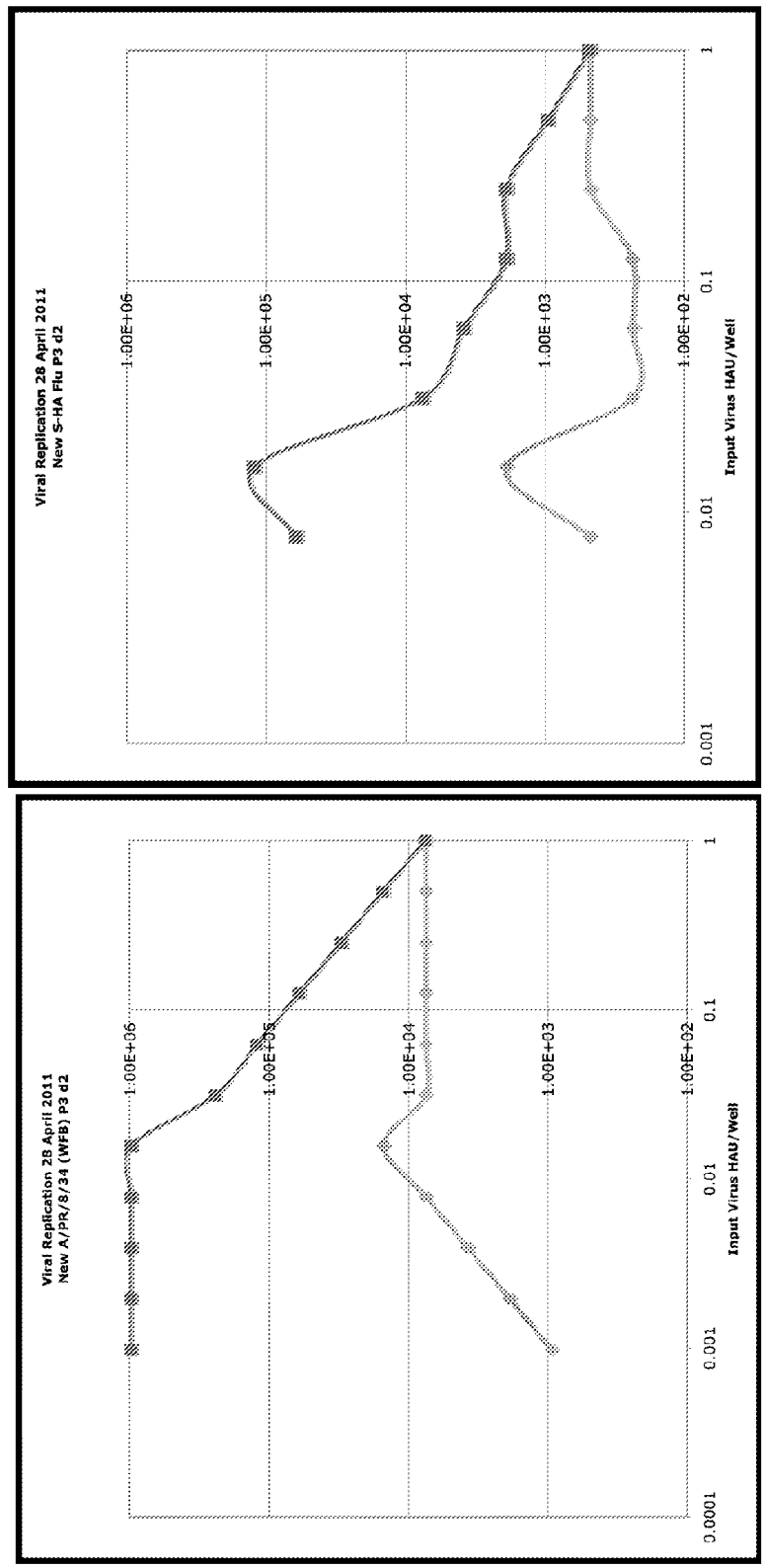

FIG. 2E—illustrates graphically the replication of the modified S-FLU influenza virus in haemagglutinin transfected cells.

Figure 3A:
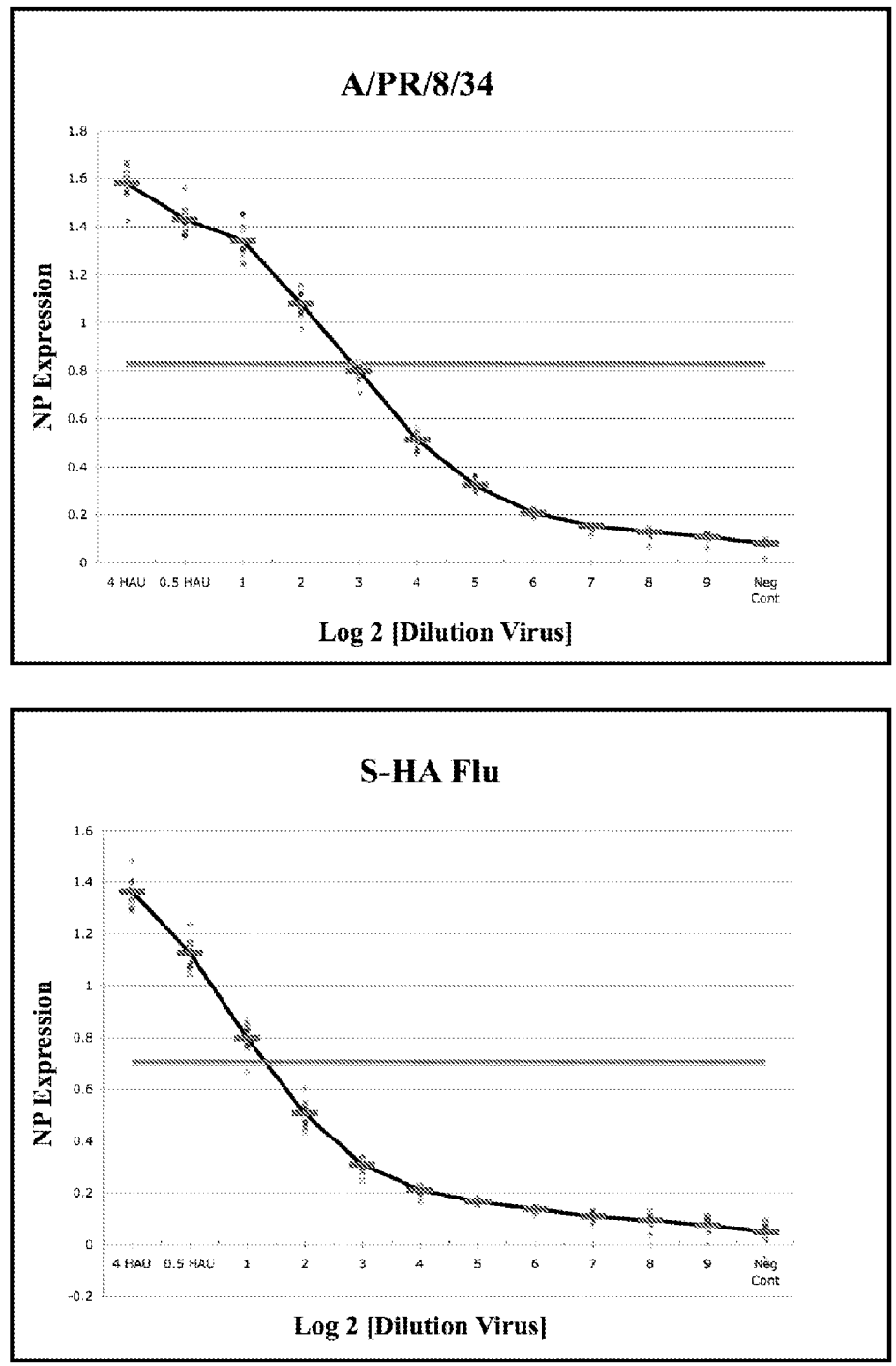

FIG. 3A—further illustrates graphically the synthesis of nucleoprotein by cells infected with the modified S-FLU influenza virus. This is in addition to the data presented in FIG. 2A.

Figure 3B:
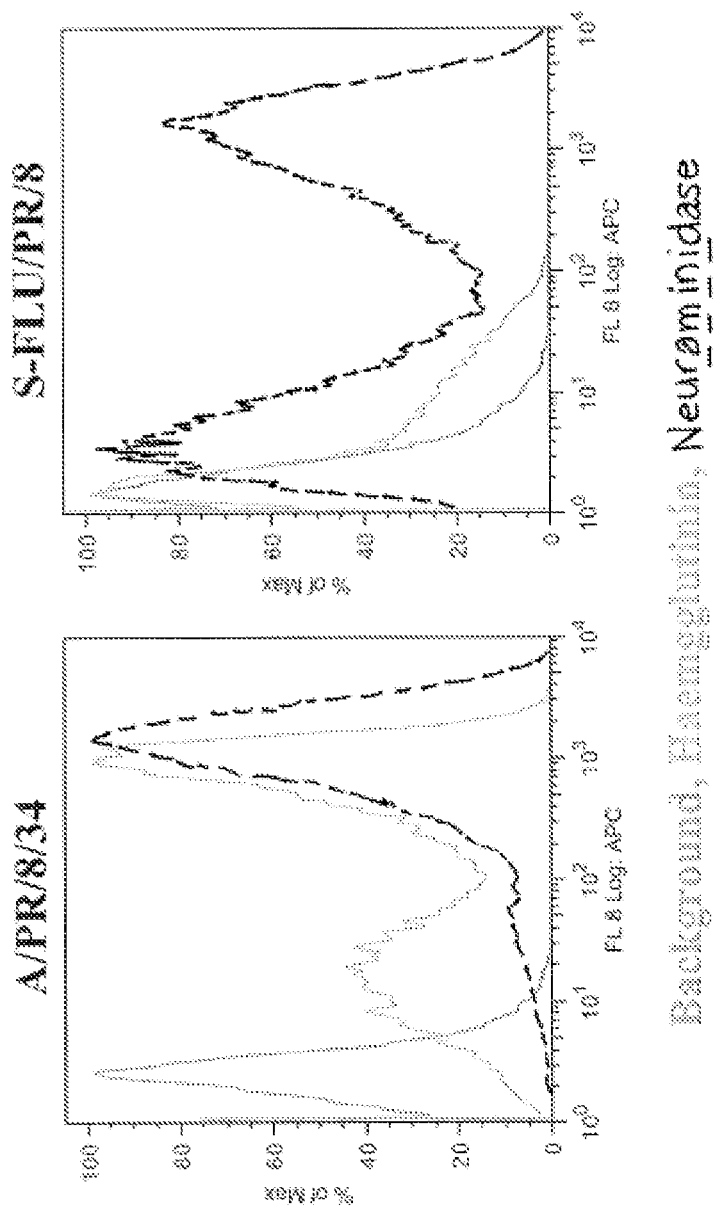

FIG. 3B—further illustrates graphically the expression of neuraminidase but not haemagglutinin in cells infected with the modified S-FLU influenza virus. This is in addition to the data presented in FIG. 2B.

Figure 3C:
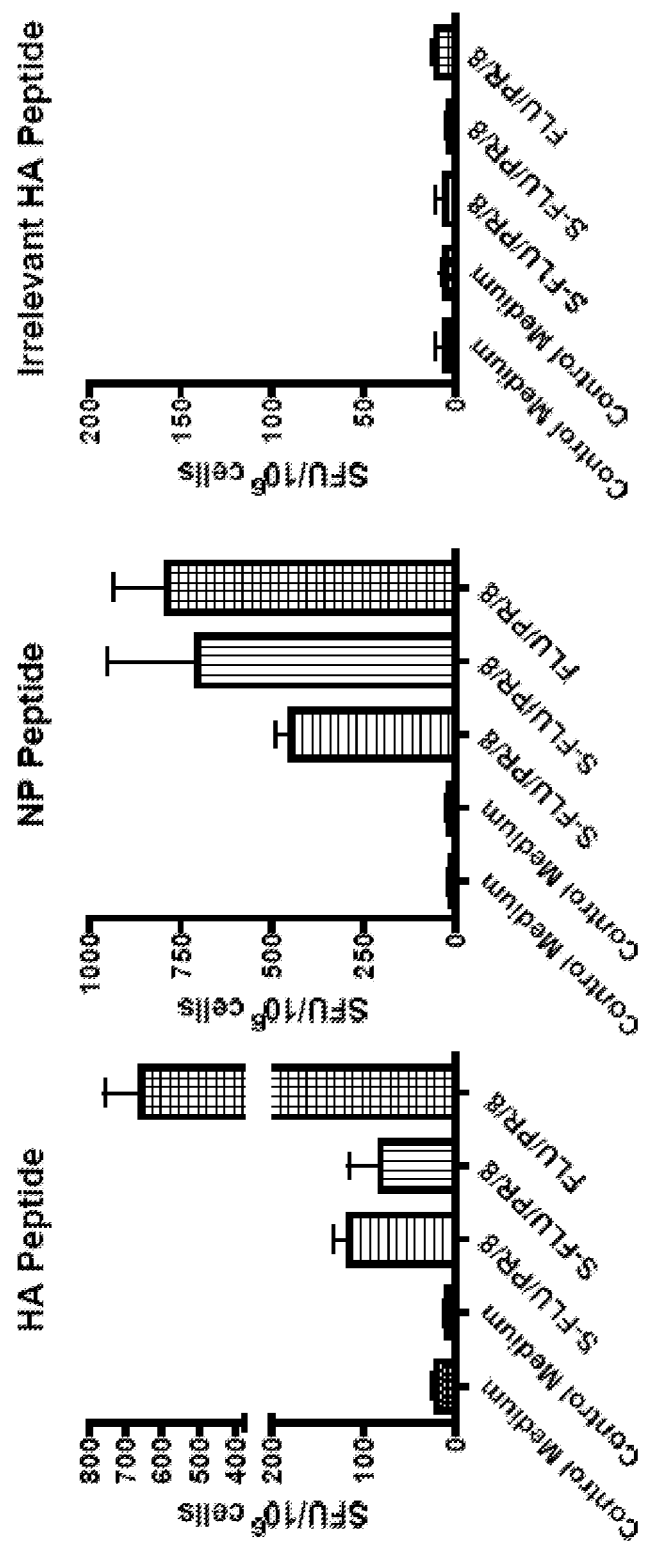

FIG. 3C—illustrates graphically that the modified S-FLU influenza virus induces nucleoprotein and haemagglutinin specific T cells as detected by ELIspot assay.

Figure 4:
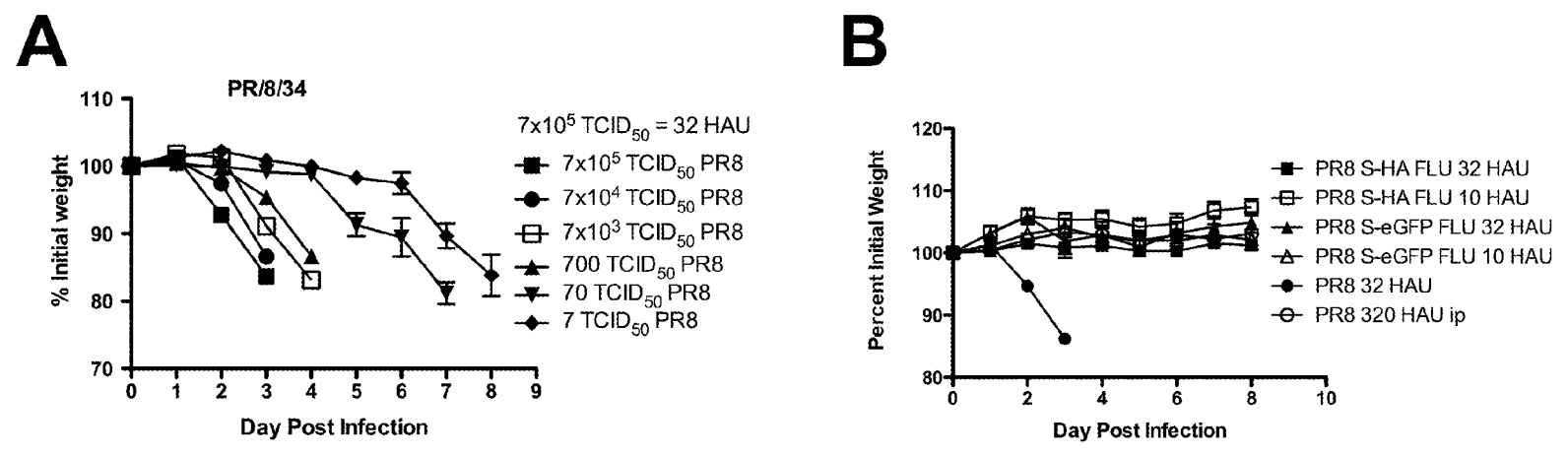

FIGS. 4A and 4B—illustrates the pathogenicity of S-FLU compared to A/PR/8/34 (Cambridge) for BALB/c Mice. Anaesthetised BALB/c mice were infected intranasally with various doses of wild-type A/PR/8/34 Cambridge Strain HA sequence (32 HAU is equivalent to $6.4\times10^5$ TCID50) n=4 per group (FIG. 4A), or the related pseudotypes S-HA FLU [S-H1(PR8)/N1(PR8)] H1(PR8) or the eGFP expressing version S-eGFP FLU [S-eGFP/N1(PR8)] H1(PR8) (FIG. 4B) and monitored for clinical symptoms and weight loss n=6 per group. Animals were euthanased if weight loss reached 20%. Data are from a representative experiment repeated three times. Values are means+/−SD.

Figure 4C:
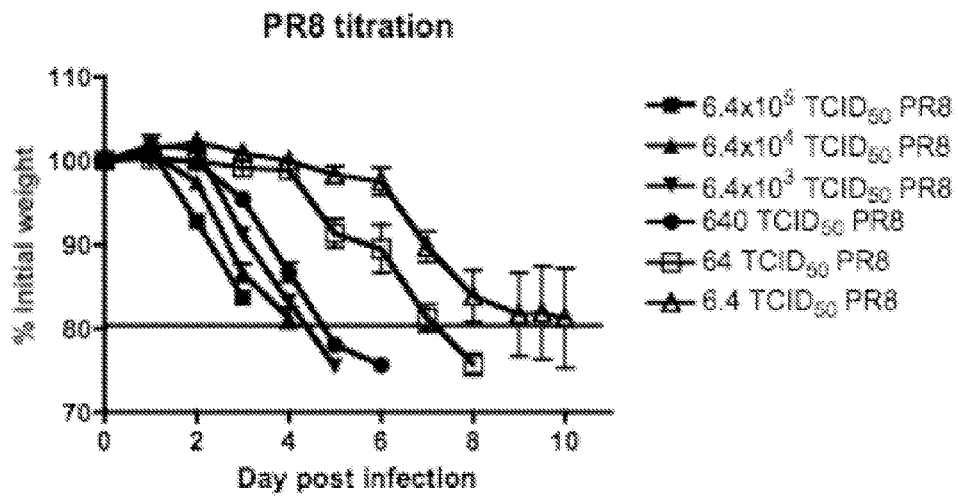

FIG. 4C—further illustrates graphically the pathogenicity of the wild influenza virus A/PR/8/34 on mice. Pathogenicity is demonstrated by monitoring weight loss in the animals. The virus is introduced intranasally.

Figure 4D:
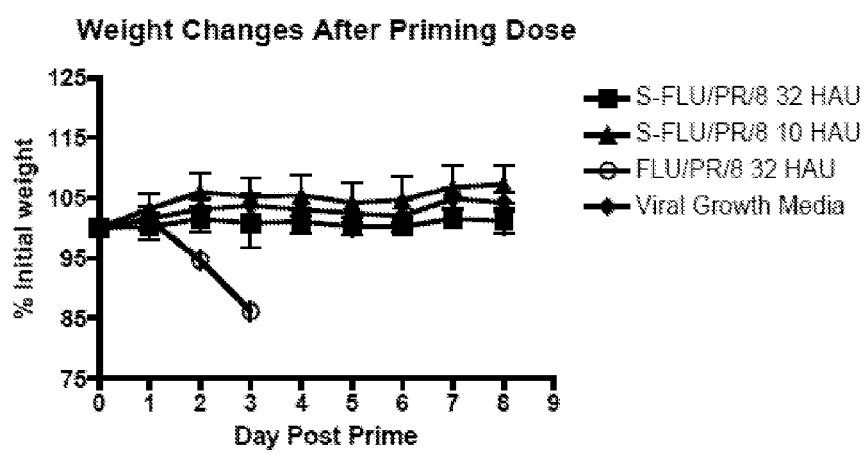

FIG. 4D—further illustrates graphically that the modified S-FLU influenza virus is not pathogenic (does not induce weight loss) when administered intranasally to mice.

Figure 5:
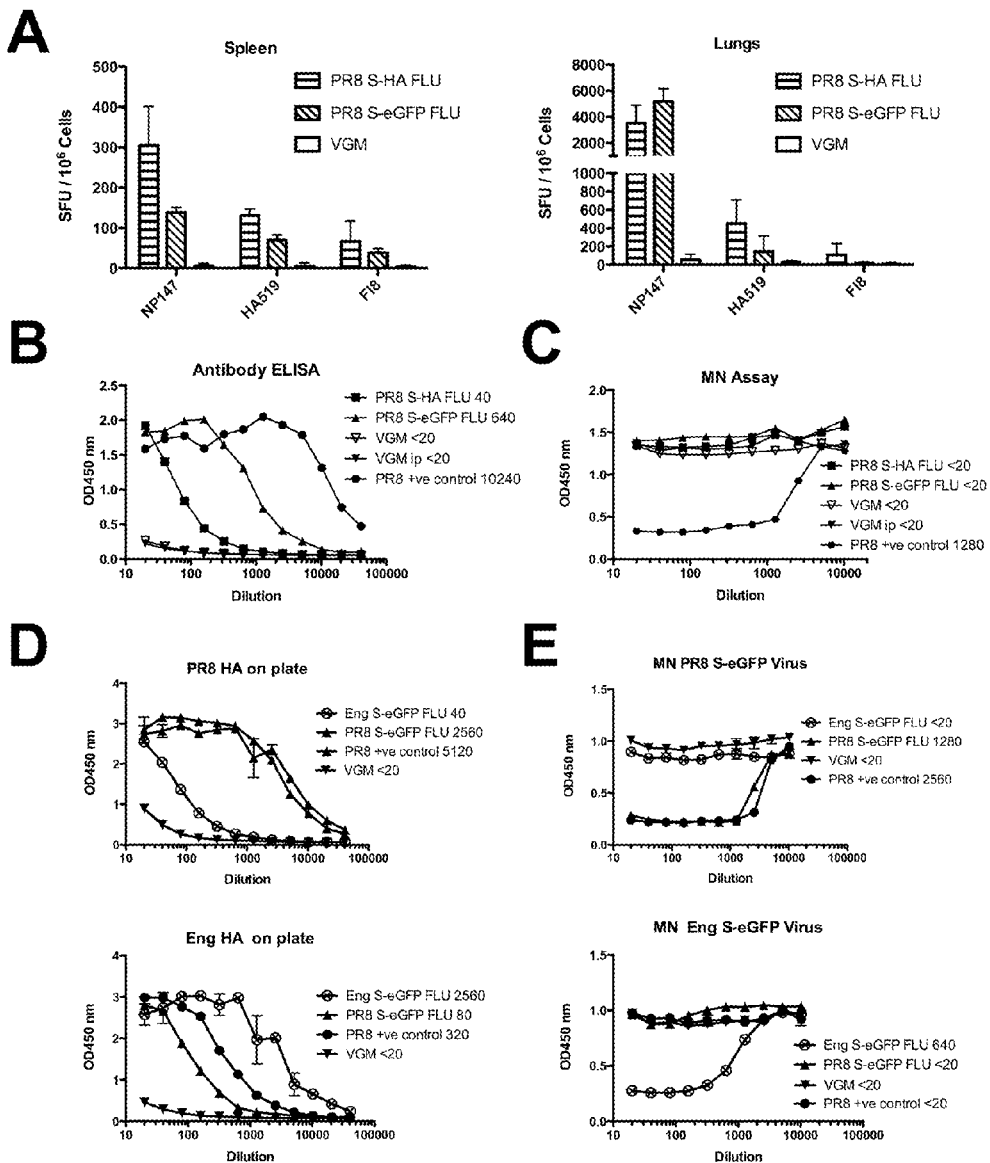

FIGS. 5A to 5D—illustrate the immune responses to S-FLU in Mice. BALB/c mice were infected intranasally with 32 HAU PR8 S-HA FLU: [S-H1(PR8)/N1(PR8)] H1(PR8), 32 HAU PR8 S-eGFP FLU: [5-eGFP/N1(PR8)] H1(PR8) or VGM on day 0 and day 14 and culled 21 days later when serum, spleens and lungs were collected. FIG. 5A: illustrates CTL specific for NP and HA detected in lung and spleen after i.n. inoculation. Pooled spleen or lungs single cell suspensions were frozen before analysis by ELISPOT. FIG. 5B: illustrates the antibody response detected in serum ELISA after 32 HAU i.n.×2. FIG. 5C: illustrates that neutralising antibody was not detected after 32 HAU×2 i.n. (D,E) BALB/c mice were immunised intraperitoneally with 320 HAU Eng S-eGFP FLU: [S-eGFP/N1(Eng195)] H1(Eng195), PR8 S-eGFP FLU: [S-eGFP/N1(PR8)] H1(PR8), WT PR/8/34 Camb virus or VGM. FIG. 5D: illustrates the antibody response after 320 HAU i.p.×2 measured by ELISA. FIG. 5E: illustrates the neutralising antibody response after 320 HAU×2 i.p. measured by MN assay. Data shown are from pooled spleen or lung cells or pooled serum and are representative experiments with n=6 repeated at least twice with similar results. Assay determinations were FIG. 5A: triplicates, FIG. 5B, 5C: duplicates or FIG. 5D, 5E: quadruplicate data shown as mean+/−SD. Titres shown are the last dilution to give >50% of plateau value.

Figure 6:
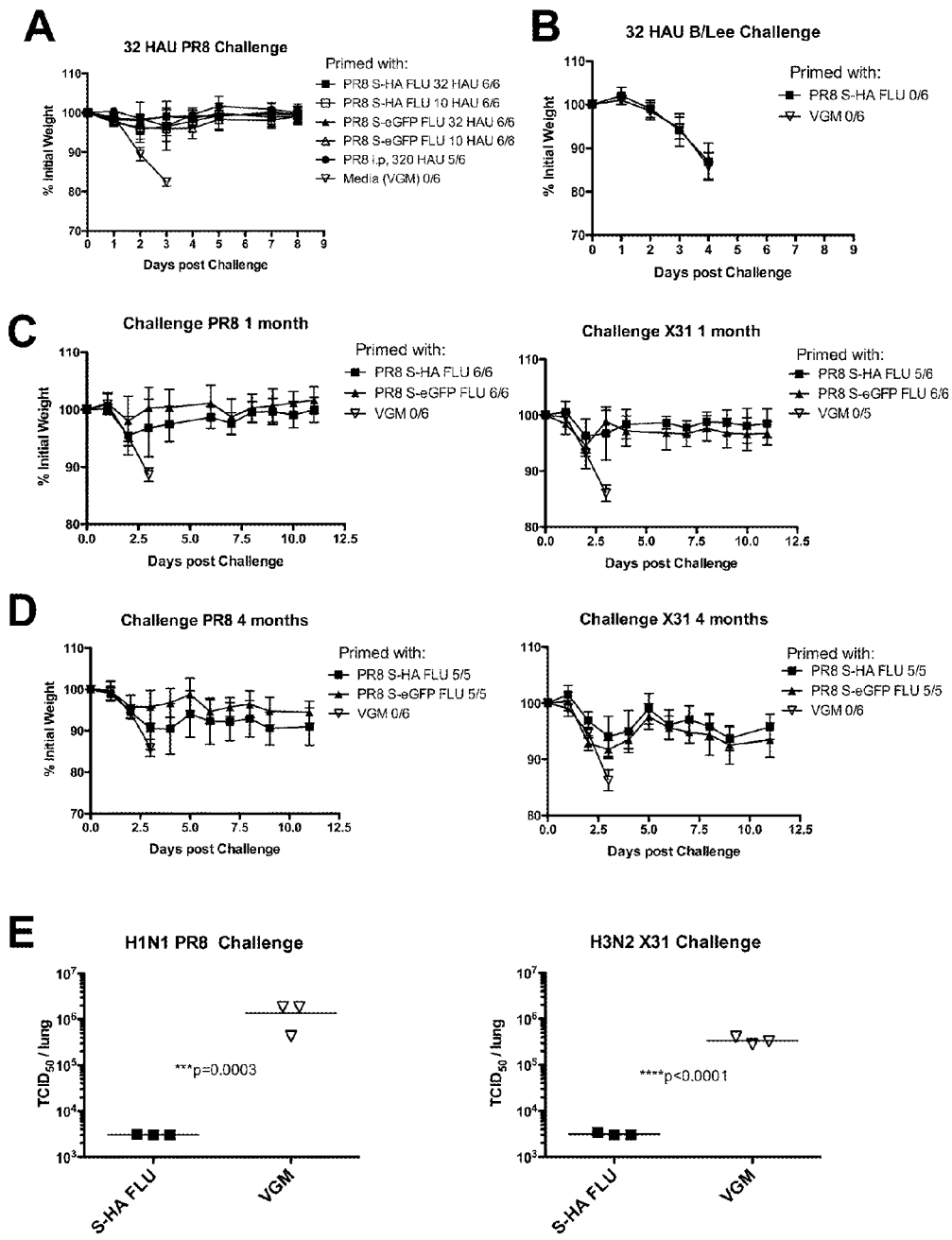

FIGS. 6A to 6E—illustrate the protection from challenge after vaccination with S-FLU. BALB/c mice were immunised with PR8 S-HA FLU: [S-H1(PR8)/N1 (PR8)] H1(PR8), PR8 S-eGFP FLU: [SeGFP/N1(PR8)] H1(PR8) or VG M at day 0 and day 14. Mice were then challenged with 32 HAU virus and weight loss and clinical score monitored for at least 10 day s. FIG. 6A: Mice were primed with 32 or 10 HAU S-HA FLU or S-eGFP FLU virus. Mice were challenged with: FIG. 6A: 32 HAU PR8 on day 28. FIG. 6B: 32 HAU B/Lee on day 46, FIG. 6C: 32 HAU PR8 or X31 virus on day 40. FIG. 6D: 32 HAU PR8 or X31 after 4 months. Figures A-D: numbers that did not lose 20% weight over number in group are shown on the legends. FIG. 6E: Day 39 challenged mice were culled at day 3 post challenge and lungs were collected and snap frozen in liq N2. TCID50 titres were then determined using SIAT-MDCK c ells and statistical differences are student's t test comparing log transformed data. Experiments were repeated at least three times with similar results and representative data is shown. Percentage initial weights shown are means+/−SD.

Figure 7:
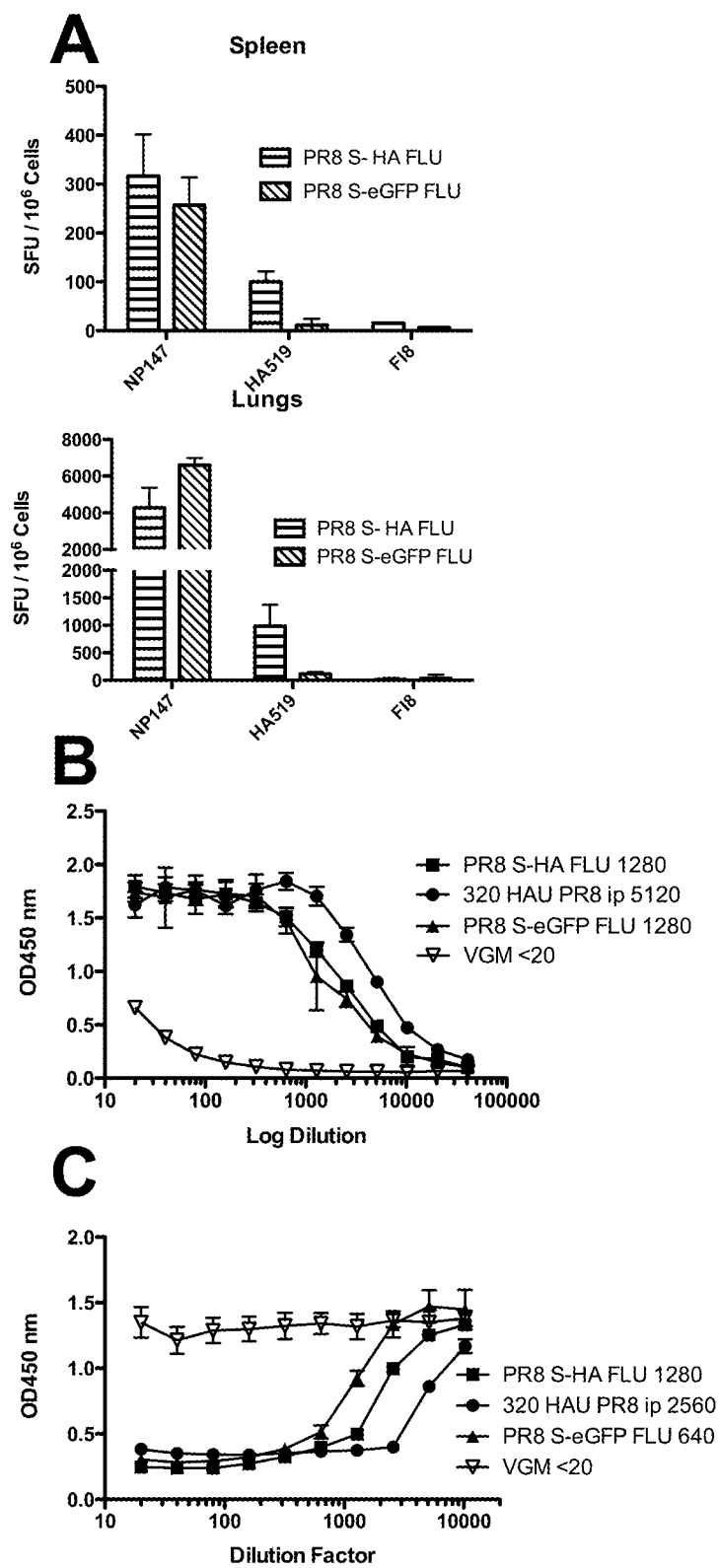

FIGS. 7A to 7C—illustrates immune responses post immunisation and challenge. BALB/c mice were immunised with 32 HAU S-HA FLU: [5-H1(PR8)/N1(PR8)] H1(PR8), S-eGF P FLU:[S-eGFP/N1(PR8)] H1(PR8) or VGM at day 0 and day 14. Mice were challenged at day 28 monitored for recovery and then culled on day 45 when spleen, lungs and serum were collected. FIG. 7A: Pooled spleen and lung single cell suspensions from 6 animals were tested in ELISPOT assays. FIGS. 7B and 7C: Pooled sera from 6 animals were tested in an ELISA (FIG. 7B) and a microneutralisation assay (FIG. 7C). Data shown are FIG. 7A: triplicates, FIG. 7B, 7C: quadruplicates+/−SD representative of at least two experiments which had similar results. Titres shown are the last dilution to give >50% of plateau value.

MATERIALS AND METHODS

Design of S-FLU (FIGS. 1A and 1B)

The HA (haemagglutinin) sequence derived from the vRNA of A/PR/8/34 Cambridge (Winter et al (1981) Nature 292:72-75, Genbank CAA24272.1) was altered by replacing the original ATG start codon with TAG (bases A33T and T34A) to suppress translation of the signal sequence. A single base at the end of the signal sequence at position 83 was removed to ensure that if the original ATG was reconstituted by back mutation it would read out of frame. Nucleotide 83 was replaced with the sequence GCGGCCGCCACCATG (SEQ ID NO: 1) that contains an idealised Kozac sequence containing a NotI site to initiate protein synthesis beyond the signal sequence, and to provide a cloning site for insertion of any desired sequence. Finally as a further safety mutation the Arg codon (1063-5 AGA) was changed to CAG to encode Gln and inactivate the HA cleavage site. This S-HA sequence was synthesised by Geneart. This construct is referred to as S-FLU.

FIGS. 1A and 1B illustrate the mutations made to the haemagglutinin gene in an example of a modified influenza virus according to the invention. The mutations that have been introduced into the haemagglutinin gene are designed to retain the RNA encoding the signal sequence to allow packaging of the virus, but tp suppress translation of the haemagglutinin signal sequence into protein.

The S-eGFP form was made by replacing the HA sequence between the introduced NotI site and an EcoRI site at position 1268 with eGFP (Clontech) ending with a stop codon to prevent expression of any downstream HA sequence, but preserving all of the sequences required for packaging the vRNA.

An additional pseudotyped S-eGFP virus was produced based on the pandemic H1N1 strain A/Eng/195/2009 in which the N1 (Genbank GQ166659.1) vRNA and surface H1 HA (Genbank ACR15621.1) from A/Eng/195/2009 replace those of A/PR/8/34. Finally a version of A/PR/8/34 with the wild type HA from the Cambridge strain (Genbank CAA24272.1) was also made.

Virus Production

The required cDNA copies of the vRNA sequences described above (e.g. S-FLU and S-eGFP) were synthesised by Geneart with SapI sites positioned at both ends and cloned into pPolISapIT between appropriate SapI sites as described by Fodor et al (1999) Journal of virology 73:9679-9682 and Subbarao et al (2006) Immunity 24:5-9. A control was also made with the unmutated HA sequence for comparison. Recombinant pseudotyped viruses were produced by standard transfection into $10^6$ 293T cells in 2 ml volume with Lipofectamine (Invitrogen) with the addition of the expression plasmid pCDNA 3.1 containing a full length coding sequence (without the 3' and 5' UTRs) for the required HA composed of humanised codons to optimise expression and complement for lack of HA expression by the virus. The full length humanised HA sequences were synthesised by Geneart.

This exogenously provided full length haemagglutinin provided surface haemagglutinin and allowed the virus particles produced to replicate.

For propagation of the wild-type control A/PR/8/34 virus was rescued by growth on MDCK-SIAT1 cells. After three passages the virus grew to a titre of 256 HAU/50 micro-liters and was frozen in aliquots.

Pseudotyped viruses, such as S-FLU, from the initial 293T transfections were propagated in MDCK-SIAT1 cells (Matrosovich et al (2003) Journal of virology 77:8418-8425) stably transduced with the lentiviral vector pHR-SIN (Demaison et al (2002) Hum Gene Ther 13:803-813) engineered to express the full length humanised HA from A/PR/8/34 or A/Eng/195/2009 and lacking 3' and 5' UT regions. Transduced cells were stained with HA specific monoclonal antibodies and FACS sorted to achieve maximal expression of HA. 1 ml of Virus supernatants from the 293T transfections were added to $5\times10^5$ cells in 1 well of a 6 well plate for 1 hr, 2 ml of DMEM/0.1% BSA containing Pen and Strep and 1 microgram/ml of TPCK treated trypsin (Sigma T-1426) was added and the virus containing s/n collected after 48 hrs incubation at 37 deg C. Control plates containing eGFP expressing viruses were inspected under UV at 48 hrs for evidence of spreading plaques (FIG. 2). Virus stocks were produced by seeding 0.5 HAU/$10^6$ cells (MOI~1:100) on appropriate HA expressing MDCK-SIAT-1 cells in the presence of trypsin as above.

Nomenclature:

In order to distinguish the various combinations of genotype and surface HA of the pseudotyped viruses we refer to the HA and NA genotype between square brackets, followed by the origin of the surface HA. Three pseudotyped viruses were produced for the work described herein: [S-HA(PR8)/N1(PR8)] H1(PR8), [SeGFP/N1(PR8)] H1(PR8), [S-eGFP/N1(Eng195)] H1(Eng195) as well as the control A/PR/8/34 with the HA from the Cambridge strain (Winter et al (1981) Nature 292:72-75).

Virus Titration (TCID50 and Hemagglutination)

Virus titrations were based on standard procedures (Matrosovich et al (2006) Virol J 3:63) with minor modifications. TCID50 on the MDCK-SIAT1 cells in 96 well flat bottomed plates was performed by serial dilution of virus containing s/n in groups of 8 wells in 200 micl volumes onto $3\times10^4$ MDCK-SIAT-1 cells. Virus growth was detected by staining the fixed (10% v/v Formalin) and permeabilised (0.5% TritonX100) monolayer for NP expression after 48 hrs at 37 degs, with murine (Abcam AA5H) or human (2-8C produced in house) monoclonal anti NP primary antibodies, and DAKO HRP labelled anti mouse (P0447) or anti Human (P0241) Ig as described (Matrosovich et al (2006) Virol J 3:63), replacing the wash solution with PBS/0.1% BSA. Wells were developed with Roche PM Blue substrate (Cat 11-484-281-001), and read at 450 nM. Positive wells were defined as giving a signal >4SD above 16 uninfected control wells. For titration of virus from infected mouse lung detection was by hemagglutination of 50 micl 0.5% human red cells. TCID50 (the dilution expected to result in 50% infected wells) was calculated as described by Reed and Muench (Price et al (2010) PloS one 5:e13162). HA titre was measured as described (Webster et al (2002) WHO Manual on Animal Influenza Diagnosis and Surveillance. World Health Organisation, Geneva) by adding 50 micl 0.5% v/v human red cells adjusted so that a 1:2 dilution gave an OD600 1.8+/−0.05 to dilutions of virus in 50 micl PBS in V bottomed 96 well plates. Hemagglutination was read at 1 hr by loss of teardrop formation after tilting the plate. Pseudotyped viruses grown in 3 ml volumes in 6 well plates of confluent transduced MDCK SIAT1 cells routinely gave HA tires 16-32 HAU/50 micl and TCID50 $0.5-2\times10^7$/ml. Wild-type A/PR/8/34 (Camb) grew to 10-20 fold higher titres.

Indirect Immunofluorescence Staining of Infected Cells

Cell lines (MDCK SIAT1 or L929) were washed once in PBS and infected at MOI~5:1 for 1 hr, then incubated overnight in complete medium (DMEM/10% FCS with Pen/Strep). Harvested cells were stained by indirect immunofluorescence with monoclonal antibodies to Hemagglutinin H9-D3 Cb13 or Neuraminidase NA2-1C1 kindly provided by J. Yewdell.

Micro Neutralisation Assay

Micro neutralisation assay was based on Rowe et al (1999) J Clin Microbiol 37:937-943 with minor modifications. Viruses were diluted in Virus Dilution Medium (VDM, DMEM/Pen+Strep/0.1% BSA (Sigma A0336) without trypsin) and titrated to give plateau expression of NP in $3\times10^4$ MDCK-SIAT1 cells after overnight infection (1-4 HAU=~2–$8\times10^4$ TCID50 per well, see FIG. 2) in 96 well flat bottomed plates. Mouse antisera were heat inactivated at 56 deg C for 30 mins and 0.22 micron filtered and pooled in equal volumes from groups of 4-6 animals. Dilutions of heat inactivated mouse sera in 50 micl starting at 1/20 were added to 50 micl of virus and incubated for 1-2 hrs at 37 deg C. $3\times10^4$ indicator MDCK-SIAT-1 cells were then added in 100 micl VDM without trypsin and incubated o/n at 37 deg. The monolayer was formalin fixed and permeabilised with triton X100 as described above and stained with human anti NP igG1 monoclonal antibody 2-8C (produced in house) and HRP labelled 2nd layer anti human Ig (Dako P0241) as above. Titres were defined as the final dilution of serum that caused >50% reduction in NP expression.

T Cell ELISPOT Assay

ELISPOT assays were performed according to standard procedures similar to that done in humans (Powell et al (2012) The Journal of infectious diseases 205:20-27) but using a mouse ELISPOT kit Mabtech (Necka Strand, Sweeden). Briefly, titrated numbers of spleen or lung single cell suspensions were incubated with 2 uM (final concentration) peptide solutions in R10. After 18-24 hours cells were discarded and plates washed and developed by addition of anti-IFN-g-biotin followed by Streptavidin alkaline phosphatase and then a Bio-Rad alkaline phosphatase substrate kit (Bio-Rad, Hemel Hempstead, UK). Spots were read using a CTL ELISPOT plate reader (CTL, Shaker Heights, USA). Negative controls were irrelevant peptide (KK restricted HA eptope) and media. Positive controls used Concanavilin A (Sigma, Poole, UK).

Animals and Immunization Schedules

Mice were bred at the BMS, University of Oxford or purchased from Harlan (Shaw Farm, Bicester). BALB/c female or C57BL/6 females were used at 6-8 weeks of age. All procedures were under authority of appropriate Personal and Project licences issued by the UK Home Office. Mice were immunized intranasally twice with S-FLU or eGFP influenza in 50 micl under anaesthesia at two weekly intervals followed by at least 14 days before challenge with PR8 virus in the same conditions. A humane endpoint of 20% weight loss was used for mice which would otherwise have succumbed to infection. Animals were also assessed for clinical score in terms of mobility, appearance and breathing intensity. Moribund mice were killed for humane reasons even if 20% weight loss was not achieved.

Production of Recombinant HA

Recombinant HA constructs were based on the design of Stevens et al (2004) Science 303:1866-1870. cDNA encoding the HA from A/PR/8/34 Cambridge (Winter et al (1981) Nature 292:72-75, Genbank CAA24272.1) or A/Eng/195/2009 (Genbank ACR15621.1) with human optimised codons was synthesised by Geneart. HA sequences up to codon 176 of HA2 (H3 numbering) were linked to the T4 fibritin trimerisation sequence and 6H for purification as described (Stevens et al (2004) Science 303:1866-1870) and subcloned into the murine retroviral vector pQCXIX (Clontech) containing an eGFP expression cassette beyond an IRES as described (Schimanski et al (2009) Blood Cells Mol Dis 43:180-193). Packaging of retrovirus, transduction and sorting of 293T cells, and HA protein purification was done as previously described with yields of 1-5 mg/liter (Schimanski et al (2009) Blood Cells Mol Dis 43:180-193). The purified HA0 gave a single dominant band of ~75 KD on coomassie stained reduced SDS polyacrylamide gels (not shown).

ELISA Assay for Antibodies to HA.

The ELISA was done as described (Harlow, E., and D. Lane. 1988. Antibodies: A Laboratory Manual. Cold Spring Harbor Laboratory), Ch 14 p 564). Briefly, flat bottomed 96 well ELISA plates (Falcon 353915) were exposed for 2 hrs to 20 micg/ml purified HA, washed ×2 in PBS and blocked with 3% BSA. After washing ×2 PBS, Mouse sera were pooled (4-7 animals), heat inactivated at 56 deg C for 30 mins, 0.22 micron filtered, and diluted from 1:20. 50 micl volumes were added to the plates for 1-2 hrs, washed ×4 with PBS and bound with 50 micl DAKO anti mouse HRP antibody (P0447 1:2000), washed ×4 then developed with 50 micl Roche PM Blue Substrate (Cat 11-484-281-001) and read at 450 nm. Titres were expressed as the last dilution to give >50% of the plateau positive signal.

Results:

Generation of S-FLU and Growth Properties In Vitro.

Two versions of S-FLU based on suppression of the hemagglutinin signal sequence were designed (FIG. 1A). The first prevents expression of full length hemagglutinin (HA) but allows for the expression of a signal deleted form of the protein (SHA) in the cytosol which is rapidly degraded and can be presented to class I restricted CTL via the cytoplasmic pathway of antigen presentation. This version was made to assess whether the addition of HA epitopes might enhance the effectiveness of S-FLU as a vaccine. This was compared to a second version in which most of the HA sequence was replaced with eGFP (S-eGFP), that is expressed in the cytoplasm of infected cells and can be visualised under UV light.

S-FLU viruses were demonstrated to infect target cells and express the viral NP as efficiently as the wild type A/PR/8/34 virus. FIG. 2A shows that [S-HA(PR/8)/N1(PR8)] H1(PR8) infects MDCK-SIAT-1 cells at MOI>1:1 (1 TCID50: 1 cell) in the absence of trypsin, and expresses NP to levels equivalent to wild-type PR8. The same was found for the S-eGFP versions based on PR/8 or the pandemic H1N1 virus A/Eng/195/2009 (data not shown).

FIG. 2B shows that replication of S-FLU is limited to MDCK-SIAT1 cells that express an appropriate hemagglutinin protein. The upper panel shows clonal expansion of [S-eGFP/N1(Eng)] H1(Eng) titrated to beyond limiting dilutions (MOI~1: $3\times10^4$) occurred only in HA transfected cells in the presence of trypsin. FIG. 2C shows this visually for the [S-eGFP/H1(PR8)] H1(PR8) which formed spreading fluorescent plaques in HA transfected cells but only single cell infections in untransfected cells. Replication was also dependent on the presence of trypsin (not shown).

Finally surface expression of HA and NA was compared after overnight infection of MDCK-SIAT1 cells with the S-FLU viruses and wild-type A/PR/8/34. FIG. 2D shows that infection with S-FLU achieves similar surface expression of NA as wild-type, suppression of the HA signal sequence prevents expression of the folded HA protein at the cell surface. Similar staining patterns were obtained after infection of murine L 929 cells (not shown). Together these results established that S-FLU can infect cells and express viral proteins but is not able to spread from cell to cell in vitro without a source of complete hemagglutinin protein in the infected cell membrane and trypsin.

This observation is further supported by the results in FIG. 2E which shows that the modified influenza virus S-FLU/PR/8 replicated in MDCK-SIAT1 cells that expressed haemagglutinin, but did not produce any haemagglutinating activity in the supernatant of wild-type MDCK-SIAT1 cells. These results demonstrate that the new Kozak sequence, replacing base 83, functions to initiate translation of the signal deficient haemagglutinin protein.

FIG. 2E further compares the replication of S-FLU/PR/8 in haemagglutinin expressing MDCK (on the right), to the replication of the control A/PR/8/34 in wild type MDCK-SIAT1 (on the left). At optimal dilution A/PR/8/34 replicates $10^6$ fold in 48 hrs. The modified influenza virus (S-FLU) replicates $10^4$ to $10^5$ fold in the same period in haemagglutinin expressing MDCK cells.

FIG. 3A compares the production of Nucleoprotein (NP) in MDCK-SIAT1 cells infected with wild type virus or modified influenza virus S-FLU. The results demonstrate that the modified influenza virus S-FLU strain can induce a similar level of NP expression as the wild-type virus. FIG. 3B (left panel) shows the expression of haemagglutinin and neuraminidase in L-cells 24 hrs after infection by wild-type A/PR/8/34. The right panel shows that the modified influenza virus S-FLU strain can induce a similar level of neuraminidase expression, but does not result in expression of folded haemagglutinin above background at the infected cell surface. FIG. 3C shows that the modified influenza virus S-FLU can induce T cells in Balb/c mice that recognise conserved peptides derived from influenza NP and from the haemagglutinin expressed in the cytosol.

S-FLU is not Pathogenic.

The pathogenicity of S-FLU was compared with wild type A/PR/8/34 expressing the Cambridge hemagglutinin in Balb/c mice. The HA from the Cambridge strain of PR/8 confers markedly increased virulence for mice through 50× greater viral replication in the lung. FIG. 4A shows that as little as 7 TCID50 (~0.00032 HAU) given in 50 micl into the nose of anaesthetised mice is enough to initiate an infection of the lung which results in clinical symptoms and weight loss to >20% (the maximum allowed). As the dose of virus is increased weight loss occurs earlier after the challenge. The route of administration of A/PR/8/34 is crucial for virulence (16), as is shown in FIG. 3B, where as much as 320 HAU given into the peritoneum does not cause any symptoms. By contrast the S-FLU viruses can be given in the maximum dose of 32 HAU into the nose of anaesthetised mice without causing any clinical symptoms or weight loss. The same results were found for C57BL/6 mice (not shown).

This observation is further supported by the data in FIGS. 4C and 4D, which shows the results of infection with S-FLU. Groups of 6 mice were anaesthetised and infected by the intranasal route with 32 or 10 Haemagglutinating Units (HAU) of the modified influenza virus S-FLU. The results were compared to animals infected with a set of 10 fold dilutions of the wild type virus starting at 32 HA units (~6.4× $10^5$ TCID50). Infected animals were monitored for weight loss and clinical score and sacrificed once 20% weight loss had occurred. FIG. 4C shows that the mice receiving wild-type virus lost weight at all of the doses given down to 6.4 TCID50, although at the lower doses there was a delay in the onset of weight loss. All mice receiving 64 TCID50 or greater doses of wild-type virus lost >20% body weight and had to be sacrificed. By contrast FIG. 4D shows that animals given modified influenza virus S-FLU did not lose any weight after either the 32 HAU dose or the lower 10 HAU dose, or show any signs of illness.

Immune Responses to S-FLU:

T Cell Responses.

Having established that S-FLU was non-pathogenic in doses up to 32 HAU given i.n. to anaesthetised mice, a vaccination regimen of two doses separated by 2 weeks was carried out. The induction of heterotypic immunity by influenza correlates well with the induction of cytotoxic T cell responses in the lower respiratory tract as opposed to the spleen or other sites. The level of class I restricted T cells was measured in the lung and spleen specific for the conserved Kd restricted NP peptide 147-158 induced by two doses of 32 HAU of S-FLU given i.n in 50 micl to anaesthetised mice. FIG. 5A shows that both versions of S-FLU induced strong NP specific responses in the lung, with about 10 fold less detectable in the spleen on a per cell basis. Similar results (not shown) were obtained in C57BL/6 mice responding to the Db restricted NP peptide 366-374. The version expressing the S-HA molecule did induce some HA specific T cells to the peptide 518-526 in Balb/c mice, but to levels about 10 fold less than NP.

Antibody Responses to S-FLU.

Antibody levels were measured in response to vaccination both by HA specific ELISA (FIG. 5B) and by Micro neutralisation (FIG. 5C). In Balb/c mice an HA specific response to vaccination i.n. was detected by ELISA, but this was not associated with neutralising activity at concentrations of serum up to 1:20. In C57BL/6 mice HA specific antibody were detected by ELISA but with minimal neutralisation at 1:20 only (not shown). By contrast pooled sera from mice immunised with a single dose of 320 HAU of A/PR/8/34 i.p., followed by challenge with 32 HAU i.n. gave a neutralising antibody titre of 1:1280.

To see if the S-FLU preparations could induce neutralising antibody when given in larger doses, two doses of 320 HAU (in 0.5 ml) were administered into the peritoneum separated by 2-3 weeks and harvested serum after three or more weeks. FIG. 5D shows that at this dose and route of administration the SFLU preparations could induce an HA specific ELISA titre to 1:2560, within 2-4 fold of that induced by A/PR/8/34 in the same dose. FIG. 5E shows that this was associated with neutralisation titres between 1:640-1:1280.

To extend this result the pandemic H1 version based on A/Eng/195/2009 was compared with the A/PR/8/34 based version. At this higher dose and route each pseudotyped virus induced a largely strain specific antibody to HA detected by ELISA, with low levels of cross-reaction (estimated at ~3% from comparing the titration curves). This was associated with neutralising antibodies to titres to 1:640-1:1280 that were strain specific with no crossneutralisation (FIG. 5E). Strain specific neutralisation was also found with antibody raised to the wild-type A/PR/8/34 after i.p. priming and 32 HAU i.n. challenge or after two doses of 320 HAU i.p. (which induced titres 1:1280-1:5120, not shown). It is note-worthy that after i.p. administration of these doses the neutralising titre induced by the S-FLU pseudotyped viruses (that cannot synthesise fresh surface HA after infection), are only 2-4 fold less than the titre induced by two doses of 320 HAU i.p. of wild type A/PR/8/34.

In several experiments at both doses no reproducible improvement in HA specific or neutralising antibody induction was observed by viruses that expressed the S-HA molecule compared to those expressing S-eGFP.

Vaccination with S-FLU Induces Homotypic and Heterotypic Immunity:

Homotypic Immunity.

To asses the protective effect of vaccination with SFLU, mice were given two doses of 32 HAU or one third of this dose ~10 HAU two weeks apart i.n. under anaesthesia and challenged with the highest dose of 32 HAU wild-type A/PR/8/34 (H1N1) or X31 (H3N2) between two weeks to 4 months later. FIG. 6A shows that both doses of S-FLU protected mice from weight loss (and clinical scores) after challenge with 32 HAU of A/PR/8/34. No difference in protective effect was seen with the virus that expressed the S-HA compared to S-eGFP. The mice vaccinated with S-FLU showed a similar level of protection as mice given a single dose of 320 HAU of the wild-type A/PR/8/34 i.p. The specificity of the protective effect for A but not B viruses is shown in FIG. 6B. As classically described (Schulman and Kilbourne (1965) J Bacteriol 89:170-174.) weight loss induced by infection with influenza B/Lee/40 is not influenced by heterotypic immunity induced to influenza A viruses.

Heterotypic Immunity to S-FLU.

These results were extended to protection by S-FLU from the heterologous strain X31 (H3N2) in FIG. 6C. The protective effect of vaccination has been repeated up to 4 months post vaccination with less than 10% weight loss after challenge (FIG. 6D). The replication of virus in the lungs of challenged mice on Day 3 of infection is shown in FIG. 6E. The titre of the heterologous virus X31 in the lungs of S-FLU vaccinated mice was reduced by ~2 orders of magnitude, whereas homologous virus was reduced 3 orders. The former result is typical of heterotypic immunity, which does not prevent infection by a second A strain virus but reduces viral replication and the associated pathology.

Post Challenge Immune Responses of Vaccinated Mice.

The level of NP and HA specific T cells in the lungs of vaccinated mice several weeks after homotypic challenge were similar in pattern and extent to those 2-4 weeks post-vaccination (FIG. 7A). Again the animals receiving the pseudotype that encoded the S-HA molecule induced a higher level of HA specific T cells. By contrast the HA specific antibody response post homotypic challenge showed a rise in titre suggestive of a secondary response, and was associated with the appearance of neutralising antibody to titres of 1:640-1:1280. Priming with the lower dose of 10 HAU S-FLU (which was fully protective) resulted in somewhat lower post challenge neutralising titres 1:160-1:320 (not shown).

This response occurred despite the lack of detectable replication of challenge virus at day 3. There was no reproducible difference in the post-challenge titres of animals vaccinated with the S-HA version compared to S-eGFP version of S-FLU.

Taken together the results show that S-FLU, a non-replicating, non-pathogenic pseudotyped influenza virus, is capable of inducing a strong local T cell response in the lung associated with classical cross-strain heterotypic immunity. In addition S-FLU can induce a strain specific neutralising antibody response if given in sufficient dose.

Discussion

The threat of pandemic influenza persists and has been emphasised by recent evidence that relatively few mutations are required in highly pathogenic H5N1 viruses to render them competent to transmit between ferrets. From a practical point of view the critical period of susceptibility for humans is between the beginning of the first wave of infection with a new pandemic strain and the distribution of matched vaccines, which at the moment is likely to be several months. A cross-protective vaccine to mitigate this first wave of a pandemic would be particularly useful.

This invention teaches the use of pseudotyped influenza viruses, that can infect but not replicate, to induce immune responses following a rigorously controlled infection of the lung. Pseudotypes can be made rapidly by standardised techniques, and incorporate any HA in the envelope, and are self replicating in vitro for bulk production. S-FLU is based on inactivation of the vRNA encoding HA, so does not contain a viable HA vRNA that could reassort with seasonal strains. Finally, given the complete control over replication, administration by small droplet aerosol to the lung might be a viable and efficient way to immunise.

The data presented herein shows that doses of the A/PR8/34 H1N1 S-FLU of 32 HAU given twice via the nose to anaesthetised mice provided solid protection from weight loss and viral replication after challenge with the homologous highly virulent parental H1N1 virus and the heterologous H3N2 strain A-X31. The high dose of the challenge and the increased virulence contributed by the Cambridge hemagglutinin were deliberately chosen to provide a convincing test for vaccination. The S-FLU vaccine at doses greater than $10^4$ fold that of the wild-type virus that induced severe weight loss, did not cause any symptoms. At the time of challenge the S-FLU vaccinated mice had a brisk cross-reactive T cell response detectable in the lung, but at this dose did not make detectable neutralising antibody in serum. This pattern of immunity was associated with marked suppression of replication of both challenge viruses in the lung, and prevented major weight loss four months post vaccination.

The heterotypic protective response induced to S-FLU that is demonstrated here is comparable to the response in mice to various influenza preparations attenuated by cold adaptation, NS deletions, HA cleavage site mutations, packaging site changes and gamma irradiation. Each of these induce heterotypic immunity with doses of ~$10^6$ or less influenza infectious units. By contrast the response to intranasal administration of recombinant non-replicating adenoviruses, capable of expressing NP and M2 proteins of influenza required a dose of ~$1 \times 10^{10}$ particles of each recombinant adenovirus to minimise weight loss in the vaccinated animals. This large difference in the dose required to achieve protection suggests that influenza particles may have properties that favour the induction of the heterotypic immune response. These might include expression of all of the core proteins in the cytosol to induce efficient antigen presentation and thus a broader repertoire of T cells. In the adenovirus experiment immunisation with either NP or M2 separately resulted in significant weight loss after challenge compared to the combination. In addition the influenza-based vaccines will introduce influenza RNA into the endosome and cytosol to initiate an innate response, which could promote a favourable adjuvant effect.

The dose of S-FLU given i.n. that promoted heterotypic immunity was also sufficient to induce a specific antibody response to hemagglutinin detectable in ELISA, but not by neutralisation (FIG. 5B). Assuming ~1000 HA spikes per virion it is calculated that this represents a dose of HA in the total inoculum of less than 1 ng. The neutralising response to a 10-fold higher dose i.p. shows that the HA in the pseudotyped virion is in a configuration favourable to the induction of neutralising antibody, albeit highly strain specific. In addition, the strong neutralising response following challenge of immunised mice suggests that the small i.n. dose may have primed for a secondary strain specific neutralising response to hemagglutinin. These results were not expected, as the amounts of HA available in the S-FLU virion are limited and cannot be amplified after infection. They suggest that this type of particle may be highly immunogenic for B cells as well as T cells. In summary the data shows that a pseudotyped, non-replicating influenza virus based on suppression of the hemagglutinin signal sequence, S-FLU, can induce heterotypic immunity and protect mice from challenge with a highly pathogenic strain of A/PR/8/34 and the heterologous H3N2 virus A-X31.

The invention claimed is:

1. A modified influenza virus wherein the RNA of the haemagglutinin gene has been modified such that the haemagglutinin signal sequence is not expressed and the virus produces a haemagglutinin protein that lacks a functional signal sequence.

2. The modified virus of claim 1 wherein the RNA is modified such that the RNA corresponding to the haemagglutinin signal sequence has at least about 60% or more sequence homology with the wild type haemagglutinin signal sequence RNA.

3. The modified virus of claim 1 wherein the influenza virus is type A.

4. The modified virus of claim 1 comprising i) a mutation in the original start codon for translation of the haemagglutinin gene such that it is no longer a start codon; and ii) the introduction of a new start codon to drive translation of the haemagglutinin gene just after the signal sequence.

5. The modified virus of claim 1, wherein the RNA of the haemagglutinin gene comprises one or more of the following:
   i) mutation of the first nucleotide of a start codon of a haemagglutinin gene and/or mutation of the second nucleotide of a start codon of a haemagglutinin gene such that the start codon is removed;
   ii) deletion of the base at the end of the signal sequence of a haemagglutinin gene;
   iii) insertion of a Kozak sequence in the place of the base at the end of the signal sequence of a haemagglutinin gene;
   iv) mutations of one or more of nucleotides 1063, 1064 and 1065 of a haemagglutinin gene to remove the cleavage site.

6. A method of preparing a modified influenza virus according to claim 1 comprising i) providing a host cell that expresses haemagglutinin with a signal sequence from a eukaryotic mRNA; and ii) providing the viral genomic nucleic acid segments for the modified virus under conditions whereby the segments are packaged into a viral particle.

7. An immunogenic composition comprising a modified influenza virus according to claim 1.

8. The immunogenic composition of claim 7 wherein the composition is capable of eliciting an immune response when administered to a human or non-human animal.

9. The immunogenic composition of claim 7 wherein the composition is suitable for intranasal administration.

10. The immunogenic composition of claim 7 wherein the composition is effective against one or more influenza strains.

11. The immunogenic composition of claim 7 comprising a further one or more antigens, in addition to the modified virus.

12. The immunogenic composition of claim 7 suitable for use as a prophylactic or a therapeutic vaccine directed to the influenza virus.

13. The immunogenic composition of claim 7 suitable for use as part of a prime boost vaccination regimen.

14. A pharmaceutical composition comprising a virus of claim 1 or a composition of claim 7 and a pharmaceutically acceptable carrier or excipient.

15. A composition comprising a modified influenza virus according to claim 1 capable of generating an immune response to influenza.

16. The composition of claim 15 wherein the immune response is prophylactic or therapeutic.

17. A method of protecting a human or non-human animal from the effects of infection by the influenza virus comprising administering to the human or non-human animal a virus according to claim 1 or a composition according to claim 7.

18. A method for raising an immune response in a human or non-human animal comprising administering a pharmaceutical composition according to claim 14 to the human or non-human animal.

19. A kit for use in inducing an immune response in an organism, comprising an immunogenic composition according to claim 7 and instructions relating to administration.

* * * * *